United States Patent
de Voir

(10) Patent No.: US 7,593,774 B2
(45) Date of Patent: Sep. 22, 2009

(54) CARDIAC PACEMAKER

(75) Inventor: Christopher S. de Voir, Tigard, OR (US)

(73) Assignee: BIOTRONIK CRM Patent AG (CH)

( * ) Notice: Subject to any disclaimer, the term of this patent is extended or adjusted under 35 U.S.C. 154(b) by 659 days.

(21) Appl. No.: 11/459,680

(22) Filed: Jul. 25, 2006

(65) Prior Publication Data

US 2008/0027498 A1 Jan. 31, 2008

(51) Int. Cl.
*A61N 1/362* (2006.01)
(52) U.S. Cl. ...................................................... 607/28
(58) Field of Classification Search .................. 607/28
See application file for complete search history.

(56) References Cited

U.S. PATENT DOCUMENTS

2007/0255329 A1* 11/2007 Bjorling ........................ 607/28

* cited by examiner

*Primary Examiner*—Carl H Layno
*Assistant Examiner*—Yun Haeng Lee
(74) *Attorney, Agent, or Firm*—Craig A. Fieschko, Esq.; DeWitt Ross & Stevens S.C.

(57) ABSTRACT

Pacemaker (10) comprises a control unit being adapted to automatically carry out a search for a capture threshold level of cardiac tissue. Available pulse strength values are tested in an iterative search wherein a next pulse strength value to be tested is determined based on Fibonacci indices.

19 Claims, 4 Drawing Sheets

| Threshold | Step 1 | Step 2 | Step 3 | Step 4 | Step 5 | Step 6 | Step 7 |
|---|---|---|---|---|---|---|---|
| 2 (0.1V) | 34 (3.3V) | 21 (2.0V) | 13 (1.2V) | 8 (0.7V) | 5 (0.4V) | 3 (0.2V) | 2 (0.1V) |
| 3 (0.2V) | 34 (3.3V) | 21 (2.0V) | 13 (1.2V) | 8 (0.7V) | 5 (0.4V) | 3 (0.2V) | 2 (0.1V) |
| 4 (0.3V) | 34 (3.3V) | 21 (2.0V) | 13 (1.2V) | 8 (0.7V) | 5 (0.4V) | 3 (0.2V) | 4 (0.3V) |
| 5 (0.4V) | 34 (3.3V) | 21 (2.0V) | 13 (1.2V) | 8 (0.7V) | 5 (0.4V) | 3 (0.2V) | 4 (0.3V) |
| 6 (0.5V) | 34 (3.3V) | 21 (2.0V) | 13 (1.2V) | 8 (0.7V) | 5 (0.4V) | 7 (0.6V) | 6 (0.5V) |
| 7 (0.6V) | 34 (3.3V) | 21 (2.0V) | 13 (1.2V) | 8 (0.7V) | 5 (0.4V) | 7 (0.6V) | 6 (0.5V) |
| 8 (0.7V) | 34 (3.3V) | 21 (2.0V) | 13 (1.2V) | 8 (0.7V) | 5 (0.4V) | 7 (0.6V) | |
| 9 (0.8V) | 34 (3.3V) | 21 (2.0V) | 13 (1.2V) | 8 (0.7V) | 11 (1.0V) | 10 (0.9V) | 9 (0.8V) |
| 10 (0.9V) | 34 (3.3V) | 21 (2.0V) | 13 (1.2V) | 8 (0.7V) | 11 (1.0V) | 10 (0.9V) | 9 (0.8V) |
| 11 (1.0V) | 34 (3.3V) | 21 (2.0V) | 13 (1.2V) | 8 (0.7V) | 11 (1.0V) | 10 (0.9V) | |
| 12 (1.1V) | 34 (3.3V) | 21 (2.0V) | 13 (1.2V) | 8 (0.7V) | 11 (1.0V) | 12 (1.1V) | |
| 13 (1.2V) | 34 (3.3V) | 21 (2.0V) | 13 (1.2V) | 8 (0.7V) | 11 (1.0V) | 12 (1.1V) | |
| 14 (1.3V) | 34 (3.3V) | 21 (2.0V) | 13 (1.2V) | 18 (1.7V) | 16 (1.5V) | 15 (1.4V) | 14 (1.3V) |
| 15 (1.4V) | 34 (3.3V) | 21 (2.0V) | 13 (1.2V) | 18 (1.7V) | 16 (1.5V) | 15 (1.4V) | 14 (1.3V) |
| 16 (1.5V) | 34 (3.3V) | 21 (2.0V) | 13 (1.2V) | 18 (1.7V) | 16 (1.5V) | 15 (1.4V) | |
| 17 (1.6V) | 34 (3.3V) | 21 (2.0V) | 13 (1.2V) | 18 (1.7V) | 16 (1.5V) | 17 (1.6V) | |
| 18 (1.7V) | 34 (3.3V) | 21 (2.0V) | 13 (1.2V) | 18 (1.7V) | 16 (1.5V) | 17 (1.6V) | |
| 19 (1.8V) | 34 (3.3V) | 21 (2.0V) | 13 (1.2V) | 18 (1.7V) | 20 (1.9V) | 19 (1.8V) | |
| 20 (1.9V) | 34 (3.3V) | 21 (2.0V) | 13 (1.2V) | 18 (1.7V) | 20 (1.9V) | 19 (1.8V) | |
| 21 (2.0V) | 34 (3.3V) | 21 (2.0V) | 13 (1.2V) | 18 (1.7V) | 20 (1.9V) | | |
| 22 (2.1V) | 34 (3.3V) | 21 (2.0V) | 29 (2.8V) | 26 (2.5V) | 24 (2.3V) | 23 (2.2V) | 22 (2.1V) |
| 23 (2.2V) | 34 (3.3V) | 21 (2.0V) | 29 (2.8V) | 26 (2.5V) | 24 (2.3V) | 23 (2.2V) | 22 (2.1V) |
| 24 (2.3V) | 34 (3.3V) | 21 (2.0V) | 29 (2.8V) | 26 (2.5V) | 24 (2.3V) | 23 (2.2V) | |
| 25 (2.4V) | 34 (3.3V) | 21 (2.0V) | 29 (2.8V) | 26 (2.5V) | 24 (2.3V) | 25 (2.4V) | |
| 26 (2.5V) | 34 (3.3V) | 21 (2.0V) | 29 (2.8V) | 26 (2.5V) | 24 (2.3V) | 25 (2.4V) | |
| 27 (2.6V) | 34 (3.3V) | 21 (2.0V) | 29 (2.8V) | 26 (2.5V) | 28 (2.7V) | 27 (2.6V) | |
| 28 (2.7V) | 34 (3.3V) | 21 (2.0V) | 29 (2.8V) | 26 (2.5V) | 28 (2.7V) | 27 (2.6V) | |
| 29 (2.8 V) | 34 (3.3V) | 21 (2.0V) | 29 (2.8V) | 26 (2.5V) | 28 (2.7V) | | |
| 30 (2.9V) | 34 (3.3V) | 21 (2.0V) | 29 (2.8V) | 32 (3.1V) | 31 (3.0V) | 30 (2.9V) | |
| 31 (3.0V) | 34 (3.3V) | 21 (2.0V) | 29 (2.8V) | 32 (3.1V) | 31 (3.0V) | 30 (2.9V) | |
| 32 (3.1V) | 34 (3.3V) | 21 (2.0V) | 29 (2.8V) | 32 (3.1V) | 31 (3.0V) | | |
| 33 (3.2V) | 34 (3.3V) | 21 (2.0V) | 29 (2.8V) | 32 (3.1V) | 33 (3.2V) | | |
| 34 (3.3V) | 34 (3.3V) | 21 (2.0V) | 29 (2.8V) | 32 (3.1V) | 33 (3.2V) | | |
| 35 (3.4V) | 34 (3.3V) | 47 (4.6V) | 42 (4.1V) | 39 (3.8V) | 37 (3.6V) | 36 (3.5V) | 35 (3.4V) |
| 36 (3.5V) | 34 (3.3V) | 47 (4.6V) | 42 (4.1V) | 39 (3.8V) | 37 (3.6V) | 36 (3.5V) | 35 (3.4V) |
| 37 (3.6V) | 34 (3.3V) | 47 (4.6V) | 42 (4.1V) | 39 (3.8V) | 37 (3.6V) | 36 (3.5V) | |
| 38 (3.7V) | 34 (3.3V) | 47 (4.6V) | 42 (4.1V) | 39 (3.8V) | 37 (3.6V) | 38 (3.7V) | |
| 39 (3.8V) | 34 (3.3V) | 47 (4.6V) | 42 (4.1V) | 39 (3.8V) | 37 (3.6V) | 38 (3.7V) | |
| 40 (3.9V) | 34 (3.3V) | 47 (4.6V) | 42 (4.1V) | 39 (3.8V) | 41 (4.0V) | 40 (3.9V) | |
| 41 (4.0V) | 34 (3.3V) | 47 (4.6V) | 42 (4.1V) | 39 (3.8V) | 41 (4.0V) | 40 (3.9V) | |
| 42 (4.1V) | 34 (3.3V) | 47 (4.6V) | 42 (4.1V) | 39 (3.8V) | 41 (4.0V) | | |
| 43 (4.2V) | 34 (3.3V) | 47 (4.6V) | 42 (4.1V) | 45 (4.4V) | 44 (4.3V) | 43 (4.2V) | |
| 44 (4.3V) | 34 (3.3V) | 47 (4.6V) | 42 (4.1V) | 45 (4.4V) | 44 (4.3V) | 43 (4.2V) | |
| 45 (4.4V) | 34 (3.3V) | 47 (4.6V) | 42 (4.1V) | 45 (4.4V) | 44 (4.3V) | | |
| 46 (4.5V) | 34 (3.3V) | 47 (4.6V) | 42 (4.1V) | 45 (4.4V) | 46 (4.5V) | | |
| 47 (4.6V) | 34 (3.3V) | 47 (4.6V) | 42 (4.1V) | 45 (4.4V) | 46 (4.5V) | | |
| 48 (4.7V) | 34 (3.3V) | 47 (4.6V) | 52 (5.1V) | 50 (4.9V) | 49 (4.8V) | 48 (4.7V) | |
| 49 (4.8V) | 34 (3.3V) | 47 (4.6V) | 52 (5.1V) | 50 (4.9V) | 49 (4.8V) | 48 (4.7V) | |

*Table IV. Sequences of the Fibonacci index and Ap amplitude for different atrial thresholds*

Fig 4

CARDIAC PACEMAKER

FIELD OF INVENTION

This invention relates generally to the design of heart stimulators for inducing a contraction of a heart chamber by way of an electrical stimulation pulse for pacing the heart if necessary. The invention relates more particularly to implantable heart stimulators like cardiac pacemakers providing automatic threshold determination.

In order to be effective, an electrical stimulation pulse needs to have a pulse strength above a capture threshold of myocardial tissue to be stimulated. A higher pulse strength generally requires a larger amount of electrical energy per stimulation pulse.

Implantable device are powered by batteries. Therefore, the life cycle of such device is limited by depletion of the battery. In case of a depleted battery, the device has to be explanted and replaced. To reduce the energy consumption of heart stimulators, state of the art heart stimulators may provide an automatic threshold search function to ensure a stimulation pulses strength at a level just above that which is needed to effectuate capture.

The heart stimulator has at least one adjustable stimulation pulse generator to generate stimulation pulses having an adjustable pulse strength for delivery to an atrium or a ventricle of the heart or both. The heart stimulator also has at least one sensing stage adapted to process electrical signals picked up by an atrial sensing electrode or a ventricular sensing electrode or both in order to detect an atrial event or a ventricular event and to generate an atrial or a ventricular sense signal upon detection of said atrial event or said ventricular event, respectively. Both, the stimulation pulse generator and the sensing stage are connected to a control unit which is adapted to respond to an output signal of the sensing stage and to trigger the generation of stimulation pulses in a respective heart chamber.

BACKGROUND OF THE INVENTION

Cardiac pacemakers are medical devices, usually implantable, that can be connected to or that are permanently connected to electrode leads for delivery of electrical stimulations pulses to the tissue (myocardium) of a human heart. Dual chamber pacemakers are capable of generating stimulation pulses for the atrium and the ventricle of a human heart. Biventricular pacemakers usually are capable to stimulate at least three chambers of a human heart that is the right atrium, the right ventricle and the left ventricle.

In a dual chamber pacemaker, this is realized by placing electrodes in both the right atrium and right ventricle of the heart.

Separate stimulation pulse generators are usually provided for each heart chamber (atrium or ventricle) to be stimulated.

A control unit is triggering the generation of a respective atrial or ventricular stimulation pulse according to a pre-programmed, variable timing regime in order to provide for adequate timing of the stimulation pulses.

A stimulation pulse to the myocardium may cause a contraction of a respective heart chamber, if the myocardium of that chamber is not in a refractory state and if the stimulation pulse has a strength above capture threshold of said myocardium. A sub-threshold stimulation pulse will not cause a cardiac contraction even if delivered to the myocardium in its non-refractory state.

Therefore, one important parameter to be adjusted in a pacemaker is capture threshold, which represents the minimum strength of a stimulation pulse required to reliably evoke cardiac contractions. This is typically determined by varying the strength (amplitude and/or duration) of applied stimulation pulses while simultaneously monitoring mechanical action or intracardiac electrical potentials produced during each contraction of the patient's heart. Capture is indicated when an applied stimulation pulse results in the occurrence of a heart contraction.

In order to determine capture threshold automatically, a heart stimulator can provide a cardiac capture threshold determination system for automatically determining the minimum pacing pulse energy required to reliably stimulate contractions of a patient's heart. The pacemaker's stimulation pulse generator is adapted to generate stimulation pulses of variable pulse strength for application to the heart, and a capture detector is provided for detecting cardiac contractions stimulated in response to the applied pacing pulses. The control unit is coupled to the stimulation pulse generator and responsive to the capture detector as to vary the pulse strength such that the pulse strength increases when the capture detector fails to detect cardiac contractions and decreases when the capture detector detects cardiac contractions.

In order to monitor the heart chamber and thus to determine whether or not a contraction of a heart chamber has occurred a pacemaker has a sensing stage for sensing a heart parameter indicating a contraction of a stimulated heart chamber.

The sensing stage can be connected to an electrode placed in a respective heart chamber. A contraction of a heart chamber can be detected by evaluating electrical potentials sensed by such sensing electrode. The time course of these potentials forms an intracardiac electrocardiogram that can be evaluated by the capture detector.

Alternatively, the sensing stage can be designed to response to the mechanical action of the heart. One way of detecting mechanical action of the heart is to evaluate an time course of intracardiac impedance.

Various alternative approaches for determining capture of a heart chamber and to discriminate an evoked response from a polarization artifact are known in the art.

Likewise, numerous approaches for providing cardiac pacemakers featuring automatic capture determination are known. One approach is disclosed in U.S. Pat. No. 4,708,142 directed to an Automatic cardiac capture threshold determination system and method However, not much effort has been put into optimization of threshold search with respect to the regime of pulse strength alteration in an iterative search. Known approaches feature stepwise reduction or increase of pulse strength until loss of capture or capture is detected, respectively.

It is an object of the present invention to provide a heart stimulator with improved automatic capture threshold adaptation.

It is a further object of the invention to provide a heart stimulator with improved capture control.

SUMMARY OF THE INVENTION

According to the present invention the object of the invention is achieved by a heart stimulator featuring a capture detector being adapted to evaluate a sensed heart parameter and to determine, whether a stimulation pulse was captured by the stimulated cardiac tissue of the heart chamber or not and to put out an output signal, said output signal being
    either a capture signal if analysis of the sensed heart parameter indicates a contraction of the heart chamber following a stimulation pulse of specific stimulation pulse strength or a non-capture signal (loss-of-capture-signal) if analysis of the sensed heart parameter indicates loss of capture, because no contraction of the heart chamber is following a stimulation pulse of specific pulse strength.

A control unit is connected to the heart stimulator's stimulation pulse generator and to said capture detector and comprises means for automatic threshold adaptation. The means for automatic threshold adaptation are configured to perform an automatic iterative threshold search wherein the lowest stimulation pulse strength leading to a capture signal is determined by stepwise increasing the adjusted pulse strength in response to a non-capture signal until and stepwise decreasing increasing the adjusted pulse strength in response to a non-capture signal. The control unit controls the stimulation pulse generator by adjusting the pulse strength according to a pulse strength value to be applied, said pulse strength value to be applied being determined by said means for automatic threshold adaptation.

According to the invention the means for automatic threshold adaptation are adapted to perform a bracketing search algorithm for automatic iterative threshold search. The bracketing search algorithm preferably is a Fibonacci search algorithm.

The Fibonacci search algorithm as presented herein may also be used to optimize a search for other pacemaker parameters like the atrioventricular delay of a dual chamber pacemaker or the interventricular of a biventricular pacemaker. However, it is best used for optimization of capture threshold search.

For capture threshold search, each available discrete pulse strength is assigned to a pulse strength index being an integer. The list of pulse strength indices is strictly monotonic increasing and any pulse strength index in the list differs from the previous or the next index by 1. An individual integer pulse strength index is unambiguously assigned to a particular pulse strength value. The list of assigned pulse strength values is strictly monotonic increasing or strictly monotonic decreasing.

Preferably the smallest pulse strength index is assigned to the smallest applicable pulse strength value resulting in both lists being strictly increasing.

Alternatively, the smallest pulse strength index can be assigned to the highest pulse strength value. In such embodiment, the list of pulse strength indices is strictly increasing, while the list of pulse strength values is monotonically decreasing.

The smallest pulse strength index preferably is 1.

The means for automatic threshold adaptation are adapted to first apply the pulse strength value being assigned to the highest Fibonacci number $rfn1_0$ in said row of integer numbers and to determine a second highest fibonacci number $rfn2_0$ and to calculate a next pulse strength index TVL as well as next iteration step parameters $Left_{n+1}$, $rfn1_{1+}1$ and $rfn2_{n+1}$ in response to the capture detector's output signal as follows:

either A: if the smallest pulse strength index is assigned to the smallest pulse strength value:

in response to a non capture signal (loss-of-capture, LOC):

$$TVL = Left_n - 1 + rfn1_n$$

$$Left_{n+1} = Left_n + rfn1_n$$

$$rfn1_{n+1} = rfn1_n - rfn2_n$$

$$rfn2_{n+1} = rfn2_n - rfn1_{n+1}$$

in response to a capture signal (CAP):

$$TVL = Left_n - 1 + rfn1_n$$

$$Left_{n+1} = Left_n$$

$$rfn2_{n+1} = rfn1_n - rfn2_n$$

$$rfn1_{n+1} = rfn1_n - rfn2_{n+1}$$

or B: if the smallest pulse strength index is assigned to the highest pulse strength value:

in response to a non capture signal (loss-of-capture; LOC):

$$TVL_n = Left_{n-1} - 1 + rfn1_{n-1}$$

$$Left_{n+1} = Left_n$$

$$rfn2_{n+1} = rfn1_n - rfn2_n$$

$$rfn1_{n+1} = rfn1_n - rfn2_{n+1}$$

in response to a capture signal:

$$TVL_n = Left_n - 1 - 1 + rfn1_{n-1}$$

$$Left_{n+1} = Left_n + rfn1_n$$

$$rfn1_{n+1} = rfn1_n - rfn2_n$$

$$rfn2_{n+1} = rfn2_n - rfn1_{n+1}$$

to apply a respective next pulse strength value being assigned to a next pulse strength index TVL pulse strength index TVL until an exit criteria is met, and to store the latest pulse strength index TVL.

According to one embodiment, the exit criteria is met if $rfn2_n$ equals 0.

According to an alternative embodiment, the exit criteria is met if the most recent pulse strength index assigned to a pulse strength value leading to capture and the most recent pulse strength index being assigned to a pulse strength value leading to non-capture are adjacent.

According to still another embodiment, the exit criteria is met if the pulse strength index TVL equals the smallest applicable pulse strength index minus one, wherein the smallest applicable pulse strength index that is a Fibonacci number.

During further operation after finishing the automatic threshold search as pointed out above, the heart stimulator will apply a pulse strength value corresponding to the stored pulse strength index TVL plus a safety margin of e.g. 0.5 Volt. An optimal safety margin is arrived at by gathering empirical data and forming a statistical distribution of the pacing threshold from measurements that are repeated closely in time. Given an alpha level, a value can be chosen that will have an infinitesimal error rate. On the other hand, choosing from standard safety margins like 0.5 V, 1.0V or 1.5V may be left to the physician.

The smallest applicable pulse strength value preferably is 0 Volt.

The step between consecutive pulse strength values is preferably 0.1 Volt. It is not necessary to provide equal steps between the threshold values to be tested. For example, step width close to 0 V can be as small as 0.1 V and my increase up to e.g. 1.0V at higher threshold levels. It is indeed a major advantage of the index-based Fibonacci search algorithm as disclosed herein that it allows for uneven steps. This is, because the algorithm relies on the indices that will still be spaced from one another by 1 even if the threshold values assigned to the indices have a different and varying spacing.

Capture detection is preferably based on evaluation of intracardiac potentials (intracardiac electrocardiogram; IEGM). Accordingly, the capture detector is preferably adapted to detect an evoked response in an electrocardiogram. However other capture detection methods and devices known to the man skilled in the art are equally applicable. Therefore, no particular capture detection algorithm is disclosed herein.

BRIEF DESCRIPTION OF THE DRAWINGS

The above and other aspects, features and advantages of the present invention will be more apparent from the following more particular description thereof, presented in conjunction with the following drawings wherein:

FIG. 4 shows a table of possible results of automatic threshold search according to the invention for a number of different thresholds

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
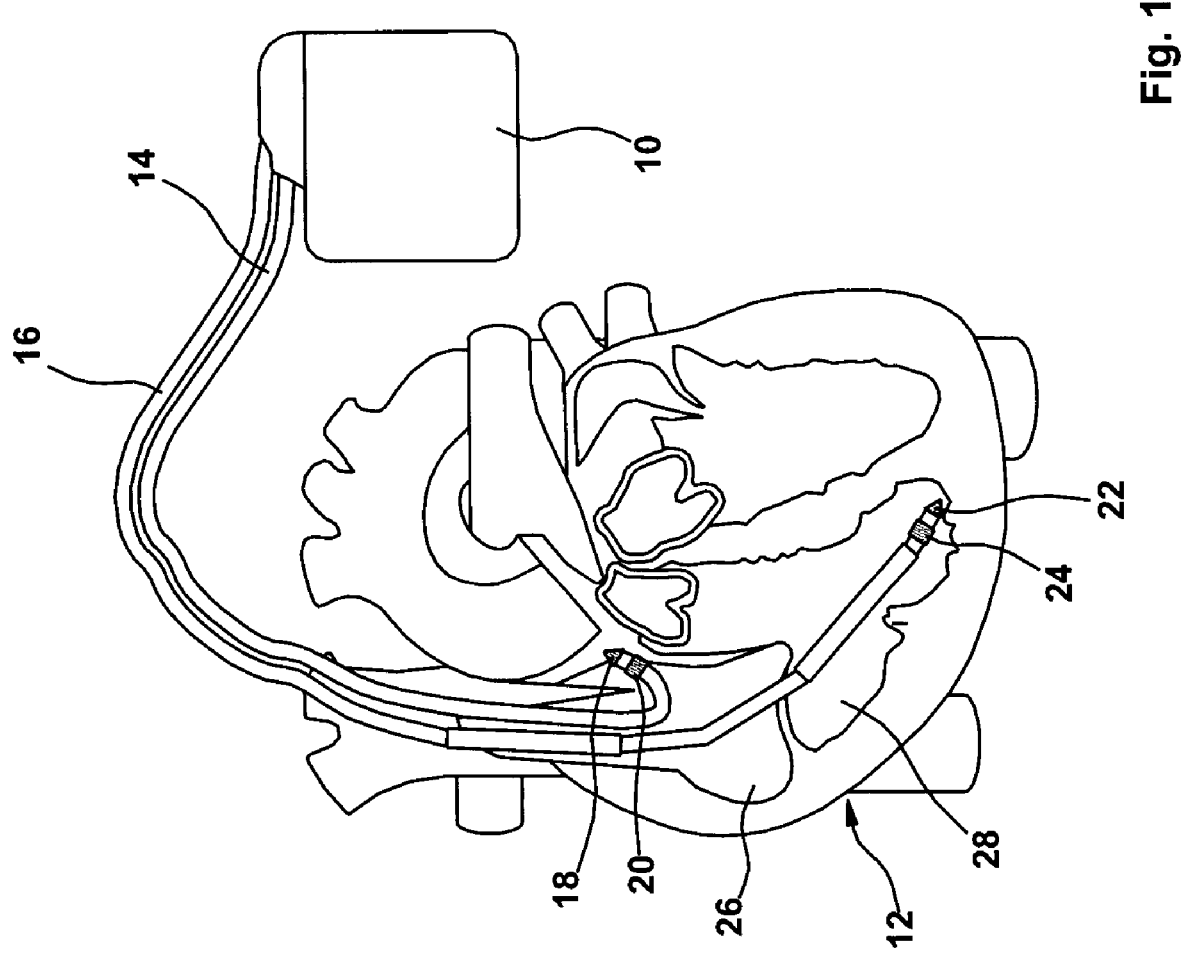
FIG. 1 shows a dual chamber pacemaker being a heart stimulator connected to leads placed in a heart.

FIG. 1 shows a dual chamber pacemaker 10 as heart stimulator connected to pacing/sensing leads placed in a heart 12 is illustrated. The pacemaker 10 is coupled to a heart 12 by way of leads 14 and 16, the lead 14 having a pair of right atrial electrodes 18 and 20 that are in contact with the right atria 26 of the heart 12, and the lead 16 having a pair of electrodes 22 and 24 that are in contact with the right ventricle 28 of heart 12. Electrodes 18 and 22 are tip-electrodes at the very distal end of leads 14 and 15, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring und electrode 24 forms a right ventricular ring electrode RV-Ring.

Figure 2:
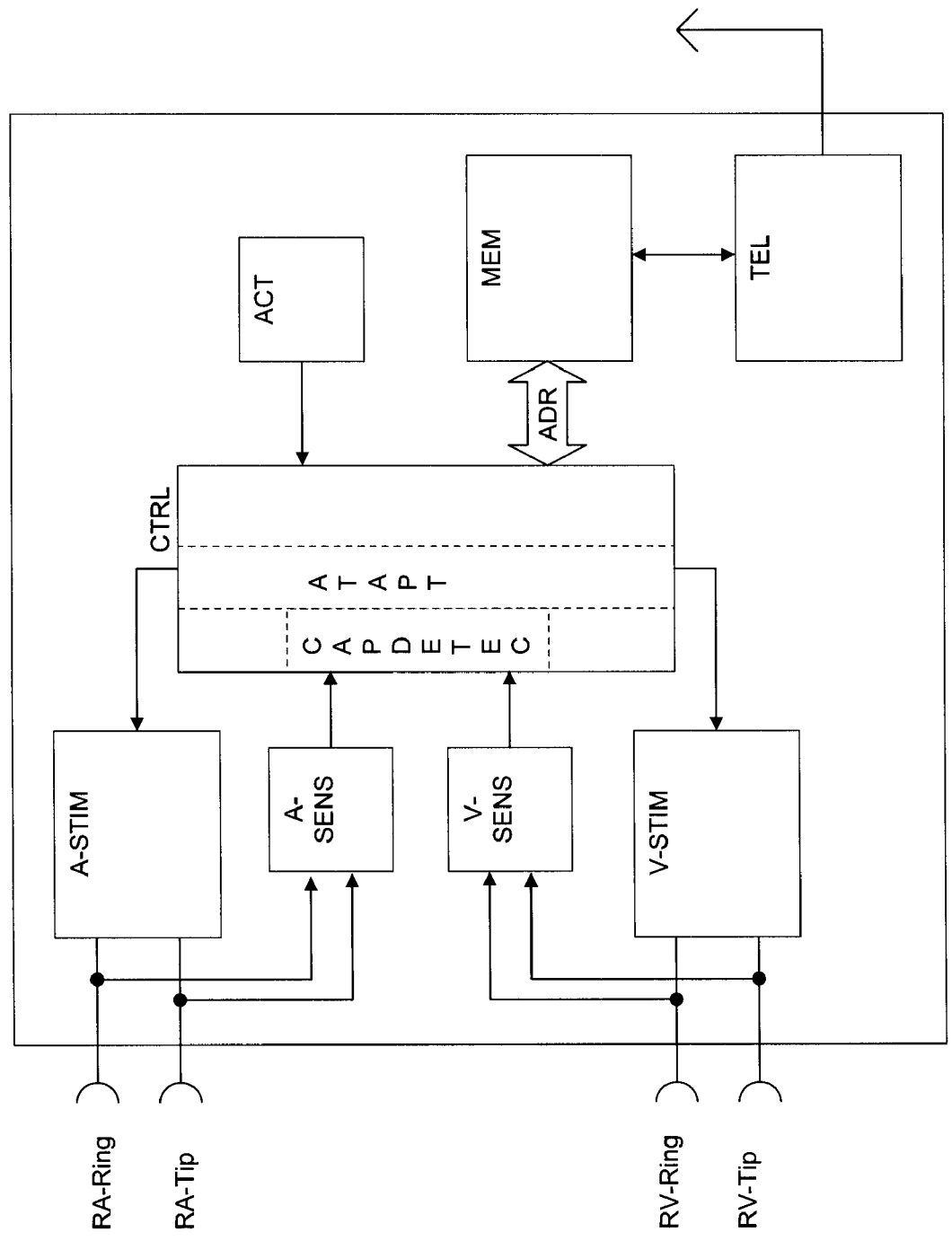
FIG. 2 shows a block diagram of a heart stimulator according to the invention.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the tip electrodes 18 and 22 from an atrial stimulation pulse generator A-STIM and a ventricular pulse generator V-STIM, respectively. Further, electrical signals from the atria are carried from the electrode pair 18 and 20, through the lead 14, to the input terminal of an atrial channel sense amplifier A-SENSE; and electrical signals from the ventricles are carried from the electrode pair 22 and 24, through the lead 16, to the input terminal of a ventricular sense channel amplifier R-SENSE.

Controlling the dual chamber pacer 10 is a control unit CTRL which is connected to the sense amplifiers A-SENSE and V-SENSE and to the stimulation pulse generators A-STIM and V-STIM. Control unit CTRL receives the output signals from the atrial sense amplifier A-SENSE and from the ventricular sense amplifier V-SENSE. The output signals of sense amplifiers A-SENSE and V-SENSE are generated each time that a P-wave or an R-wave, respectively, is sensed within the heart 12.

Control unit CTRL also generates trigger signals that are sent to the atrial stimulation pulse generator A-STIM and the ventricular stimulation pulse generator V-STIM, respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or V-pulse is being delivered to the heart, the corresponding sense amplifier, A-SENSE and/or R-SENSE, is typically disabled by way of a blanking signal presented to these amplifiers from the control unit CTRL, respectively. This blanking action prevents the sense amplifiers A-SENSE and V-SENSE from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Control unit CTRL further controls the intensity of triggered stimulation pulses by adjusting pulse strength of stimulation pulses. In the preferred embodiment, pulse strength may vary between 0.1 Volt and 5.0 Volt. Each pulse strength in a linear scale between 0.1 Volt and 5.0 Volt is unambiguously assigned to an integer between 1 and 50, each integer forming an individual pulse strength index. Intensity of triggered stimulation pulses is controlled via pulse strength indices.

Control unit CTRL comprises a capture detection module acting as capture detector CAPDETEC. Capture detector CAPDETEC is adapted to evaluate a an intracardiac electrocardiogram IEGM derived from the time course of myocardial potentials picked up by the sense amplifiers A-SENSE or V-SENSE depending on whether the capture threshold for the atrium or the ventricle is to be determined. Capture detector CAPDETEC is adapted to respond to detection of an IEGM signal corresponding to an evoked response. An evoked response is a typical time course of myocardial potentials in response to an effective electric stimulation of the myocardium evoked by a stimulation pulse.

The capture detector CAPDETEC evaluates the respective atrial or ventricular IEGM in a predetermined evaluation time window after an atrial or a ventricular stimulation pulse, respectively. Each stimulation pulse has a pulse strength assigned to a pulse strength index. Each pulse strength index is an integer.

Depending on the result of evaluation of the IEGM the capture detector CAPDETEC generates either a capture signal CAP indicating an effective stimulation pulse having a pulse strength above capture threshold or a non-capture signal LOC (loss-of-capture) if the preceding stimulation pulse was not effective and has not caused capture.

The output signal of the capture detector CAPDETEC is fed to a further module of control unit CTRL forming means for automatic threshold adaptation ATAPT. Said means for automatic threshold adaptation ATAPT are adapted to perform an automatic threshold search wherein a pulse strength value is decreased in response to a capture signal CAP and is increased in response to a non-capture signal LOC until threshold search has come to an end.

Figure 3:
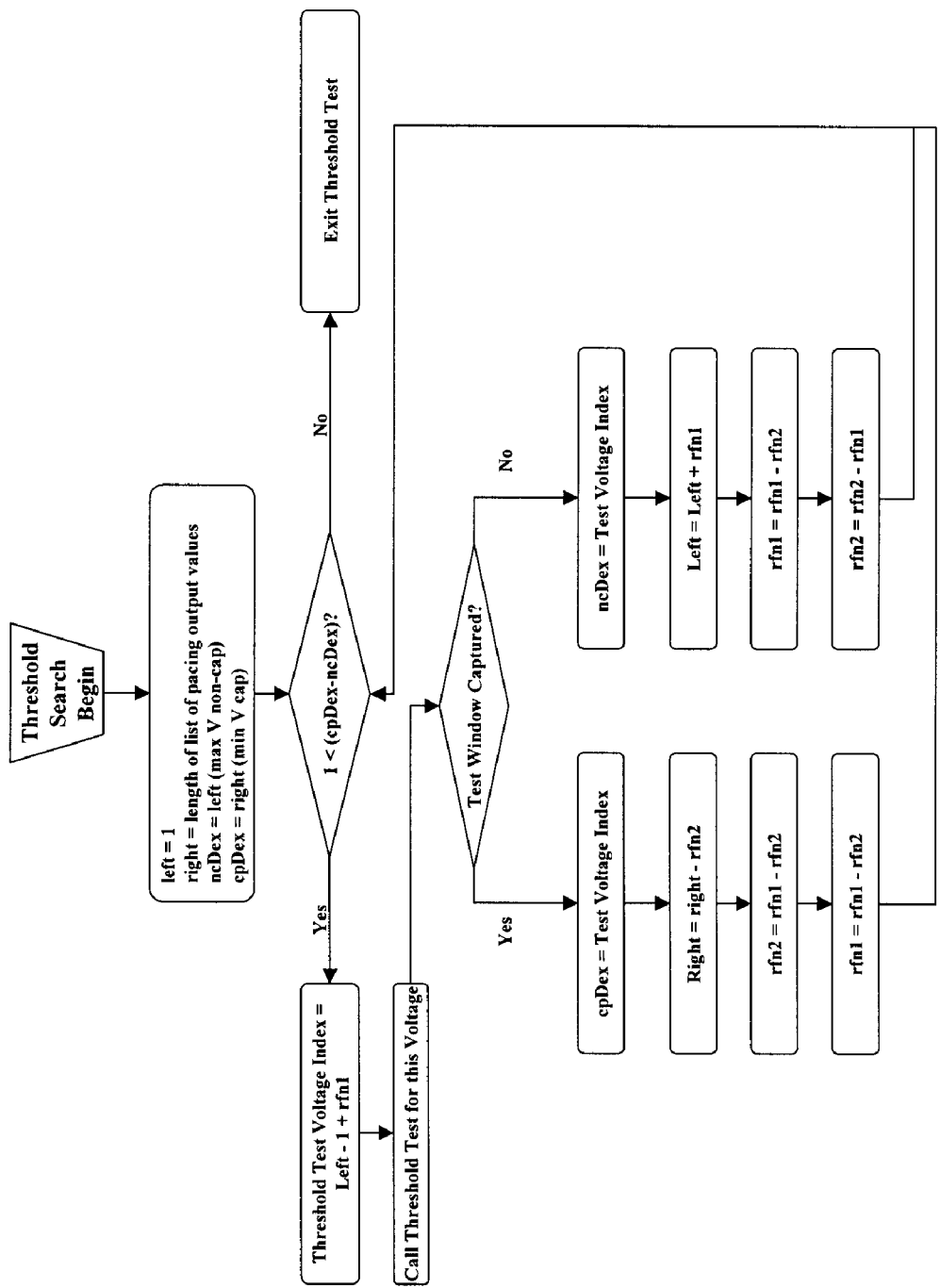
FIG. 3 shows a flow chart illustrating the operation of the control unit of the heart stimulator forming means for automatic threshold adaptation.

In order to perform a most effective threshold search, the step by which a pulse strength value is decreased or increased, respectively, is determined in a particular Fibonacci search algorithm as disclosed in more detail with respect to FIGS. 3 and 4.

Still referring to FIG. 2, the pacer 10 may also include a memory circuit MEM that is coupled to the control unit CTRL over a suitable data/address bus ADR. This memory circuit MEM allows certain control parameters, used by the control unit CTRL in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in the pacemaker 10. This telemetry circuit TEL is connected to the control unit CTRL by way of a suitable command/data bus. Telemetry circuit TEL allows for wireless data exchange between the pacemaker 10 and some remote programming or analyzing device which can be part of a centralized service center serving multiple pacemakers.

Thus, a change of capture threshold level can be remotely reported to a service center by the pacemaker 10. Also, capture threshold search as disclosed herein can be triggered from a remote central service center.

In a preferred embodiment, the pacemaker will initiate a capture threshold search periodically after a predetermined period of time.

The pacemaker 10 in FIG. 1 is referred to as a dual chamber pacemaker because it interfaces with both the right atrium 26 and the right ventricle 28 of the heart 10. Those portions of the pacemaker 10 that interface with the right atrium, e.g., the lead 14, the P-wave sense amplifier A-SENSE, the atrial stimulation pulse generator A-STIM and corresponding portions of the control unit CTRL, are commonly referred to as the atrial channel. Similarly, those portions of the pacemaker 10 that interface with the right ventricle 28, e.g., the lead 16, the R-wave sense amplifier V-SENSE, the ventricular stimulation pulse generator V-STIM, and corresponding portions of the control unit CTRL, are commonly referred to as the ventricular channel.

In order to allow rate adaptive pacing in a DDDR mode, the pacemaker 10 further includes a physiological sensor ACT that is connected to the control unit CTRL of the pacemaker 10. While this sensor ACT is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Now, the operative behavior of the pacemaker according to the invention shall be described. This behavior is achieved by adapting control unit CTRL to behave as described hereinafter.

For the purpose of this disclosure, the following abbreviations and definitions are used:

LOC: non-capture signal; loss-of-capture signal. Put out by the capture detector in case no capture is detected.

CAP: capture signal. Put out by the capture detector in the case capture is detected.

$TVL_n$: pulse strength index for Test Voltage Level; stepwise adapted during threshold search and used as pointer to the pulse strength value to be test in the n-th search step;

Left: The index of the lowest pulse strength value remaining to search in the list of available pulse strength values. The index is used as pointer to;

Right: The index of and pointer to the highest pulse strength value remaining to search in the list of available pulse strength values;

ncDex: The pointer to the maximum LOC value.

cpDex: The pointer to the minimum CAP value.

rfn1 and rfn2: Two values that always add to a Fibonacci number. These two values are recalculated using each other with each step of the search, thus resulting in two new Fibonacci numbers.

The threshold test is based on a list of available pulse strength values TVL to be tested. A pulse strength value defines a voltage of a respective stimulation pulse. Every individual pulse strength value in the list is assigned to a characteristic pulse strength index. Each index is an integer. All available pulse strength indices form a monotonic index list wherein each index differs from a neighboring index by 1.

Classification of a sequence of several test pulse strength values is required to perform the threshold search. The threshold search converges on a physiologic capture threshold when the search steps reach the minimum resolution of available pacing amplitudes. In other words, the search is complete when minimum TVL leading to CAP and the maximum TVL leading to LOC are adjacent in the list of available pulse strength values.

The search method has a mechanism of delimiting the extrema of a list of pulse strength values and choosing the next value to test in the search. The rationale for using the 'Fibonacci' search method is that it has a high efficiency and exhibits a high consistency in execution time even if thresholds vary from measurement to measurement.

A Fibonacci series is an integer series with the property that the next element in the series in the sum of the preceding two integers. For example the first eleven members of a Fibonacci series are 0, 1, 1, 2, 3, 5, 8, 13, 21, 34, and 55. The Fibonacci series also has the property that smaller Fibonacci numbers are retrievable from larger Fibonacci numbers by taking the larger Fibonacci number and subtracting a smaller Fibonacci number from it. For Example F(9) can be retrieved by subtracting F(10) from F(11): 21=55−34. Because Fibonacci numbers are integers they can be used as indices to a list of pulse strength values TVL. The retrieval property is used to search progressively smaller regions of the list as progressively smaller Fibonacci numbers are retrieved. The Fibonacci search algorithm has an exit criteria, when some minimum resolution in step change has been reached. This is demonstrated by way of various examples in FIG. 4.

FIG. 3 is flow chart of the capture threshold search algorithm according to the invention. In general a non-linear threshold search operates as follows: When the threshold search begins, Indices Left and Right bracket a list of pacing output amplitude values that is as yet unexplored. As the search progresses, the Left and Right indices are adjusted to enclose a progressively smaller region of the list. When a test value TVL returns CAP, that value and all higher values are removed from further consideration in the search. Thus the Right index is adjusted. The same is done with the Left index in case of LOC. LOC causes that value and all below to be removed from further examination.

The key feature of the Fibonacci search method according to the invention is the way the next test value TVL is chosen. The Left and Right pointers refer to indices, that is, the integer position of the highest and the lowest pulse strength value in the list of pulse strength values yet to be tested. The length of the list pulse strength values bounded by Left and Right is always related to a Fibonacci number. Therefore calculating new bounds for the remaining values to search always results in a new Fibonacci number.

Referring to FIG. 3, the Fibonacci threshold search is initialized as follows:

Left: The pointer to the lowest value remaining to search, e.g. 1.
Right: The pointer to the highest value remaining, e.g. 49.
ncDex: The pointer to the maximum LOC value; to be assigned during search.
cpDex: The pointer to the minimum CAP value; to be assigned during search.
rfn1 and rfn2: Highest and second highest Fibonacci number in the list of pulse strength indices, e.g. rfn1=34 and rfn2=21, if the list of pulse strength indices spans from 1 to 49.

The smallest pulse strength index is 1 and is assigned to the lowest available pulse strength value.

After initialization, the capture threshold search operates as illustrated in FIG. 3. Control unit CTRL is programmed accordingly. Initially, it checks if ncDex and cpDex are adjacent values, since that would be the exit condition for the search. If not, index TVL being a pointer to the pulse strength value (test voltage level) to be tested for capture is calculated based on the left hand pointer and the Fibonacci number rfn1:

$$TVL_{n+1} = Left_n - 1 + rfn1_n$$

Depending on whether application of said pulse strength value leads to CAP or LOC, index Left is adjusted to remove lower values from further consideration. Index Right is actually not used.

In response to a LOC signal indicating loss-of-capture (non-capture) for the pulse strength value assigned to TVLn just tested:

$$Left_{n+1} = Left_n + rfn1_n$$

In response to a CAP signal indicating loss-of-capture (non-capture) for the pulse strength value assigned to TVLn just tested:

$$Left_{n+1} = Left_n$$

The two Fibonacci numbers rfn1 and rfn2 are recalculated into 2 new Fibonacci numbers:

In response to a LOC signal indicating loss-of-capture (non-capture) for the pulse strength value assigned to $TVL_n$ just tested:

$$rfn1_{n+1} = rfn1_n - rfn2_n$$

$$rfn2_{n+1} = rfn2_n - rfn1_{n+1}$$

In response to a CAP signal indicating loss-of-capture (non-capture) for the pulse strength value assigned to $TVL_n$ just tested:

$$rfn2_{n+1} = rfn1_n - rfn2_n$$

$$rfn1_{n+1} = rfn1_n - rfn2_{n+1}$$

The threshold search iterates until the minimum captured value and the maximum non-captured value are adjacent. Then, the exit condition is reached:

$$1 < cpDex - ncDex$$

cpDex and ncDex are assigned and updated during search as follows:

In the case of CAP:

$$cpDex = TVLn$$

In the case of LOC:

$$ncDex = TVLn$$

To further illustrate the operation of the control unit's means for automatic iterative threshold search by way of example, it is assumed that the range of available pulse strength values is from 0.1 Volt to 5.0 Volt in steps of 0.1 Volt. Accordingly the list of pulse strength indices is including all integers between 1 and 50.

Under this conditions and further assuming a capture threshold between 0.9 V and 1.0 V, the iterative threshold search runs as follows:

| STEP 0 (initial condition): | Right = 50 | | | |
| --- | --- | --- | --- | --- |
| | Left = 1 | | | |
| | $rfn1_0$ = max FibonacciNo | | 34 | |
| | $rfn2_0$ = 2nd max FibonacciNo | | 21 | |
| | $TVL_1$ = Left − 1 + $rfn1_0$ = $rfn1_0$ = 34 | | | |
| STEP 1: $TVL_1$-> capture | | cpDex = 34 | $Right_1$ = 50 − $rfn2_0$ = 29 | $Left_1$ = 1 |
| $rfn2_2$ = $rfn1_0$ − $rfn2_0$ = 13 | | $rfn1_2$ = $rfn1_0$ − $rfn2_1$ = 21 | $TVL_2$ = 21 | |
| STEP 2: $TVL_2$-> capture | | cpDex = 21 | $Right_2$ = 29 − $rfn2_1$ = 16 | Left = 1 |
| $rfn2_3$ = 8 | | $rfn1_3$ = 13 | $TVL_3$ = 13 | |
| STEP 3: $TVL_3$-> capture | | cpDex = 13 | $Right_3$ = 16 − 8 = 8 | Left = 1 |
| $rfn2_4$ = 5 | | $rfn1_4$ = 8 | $TVL_4$ = 8 | |
| STEP 4: $TVL_4$-> noncapture | | cpDex = 13   ncDex = 8 | $Right_4$ = 8 | Left = 1 + $rfn1_4$ = 9 |
| $rfn1_5$ = $rfn1_4$ − $rfn2_4$ = 3 | | $rfn2_5$ = $rfn2_4$ − $rfn1_5$ = 2 | $TVL_5$ = 9 − 1 + 3 = 11 | |
| STEP 5: $TVL_5$ = -> capture | | cpDex = 11   ncDex = 8 | $Right_5$ = 8 − 1 = 7 | $Left_5$ = 9 |
| $rfn2_6$ = $rfn1_5$ − $rfn2_5$ = 1 | | $rfn1_6$ = $rfn1_5$ − $rfn2_6$ = 2 | $TVL_6$ = 9 − 1 + 2 = 10 | |
| STEP 6: $TVL_6$- > capture | | cpDex = 10 = ncDex = 8 | Right = 7 − 1 = 6 | Left = 9 |
| $rfn2_7$ = $rfn1_6$ − $rfn2_6$ = 1 | | $rfn1_7$ = $rfn1_6$ − $rfn2_7$ = 1 | $TVL_7$ = 9 − 1 + 1 = 9 | |
| STEP 7: $TVL_7$-> noncapture | | cpDex = 10   ncDex = 9 | $Right_7$ = 6 | $Left_7$ = 9 + 1 = 10 |
| $rfn2_8$ = $rfn1_7$ − $rfn2_7$ = 0 | | $rfn1_8$ = $rfn1_7$ − $rfn2_8$ = 1 | cpDex − ncDex = 1 -> EXIT | |

Assuming a capture threshold between 0.9 V and 1.0 V and a range of available pulse strength values between 0.1 V and 5.5 V:

| | | | | |
|---|---|---|---|---|
| STEP 0 (initial condition): | Right = 55 | | | |
| | Left = 1 | | | |
| | cpDex = 55 | | | |
| | ncDex = 1 | | | |
| | $rfn1_0$ = max FibonacciNo | 34 | | |
| | $rfn2_0 = 2^{nd}$ max FibonacciNo | 21 | | |
| | $TVL_1$ = Left − 1 + $rfn1_0$ = $rfn1_1$ = 34 | | | |
| STEP 1: $TVL_1$-> capture | cpDex = 34  ncDex = 1 | $Right_1$ = 55 − $rfn2_0$ = 34 | $Left_1$ = 1 |
| $rfn2_1 = rfn1_0 − rfn2_0 = 13$ | $rfn1_1 = rfn1_0 − rfn2_1 = 21$ | | |
| $TVL_2$ = Left − 1 + $rfn1_1$ = $rfn1_1$ = 21 | | | |
| STEP 2: $TVL_2$-> capture | cpDex = 21  ncDex = 1 | $Right_2$ = 34 − $rfn2_1$ = 21 | Left = 1 |
| $rfn2_2 = 8$ | $rfn1_2 = 13$ | $TVL_3 = 13$ | |
| STEP 3: $TVL_3$-> capture | cpDex = 13  ncDex = 1 | $Right_3$ = 21 − 8 = 13 | Left = 1 |
| $rfn2_3 = 5$ | $rfn1_4 = 8$ | $TVL_4 = 8$ | |
| STEP 4: $TVL_4$-> noncapture | cpDex = 13  ncDex = 8 | Right = 13 | Left = 1 + $rfn1_4$ = 9 |
| $rfn1_4 = rfn1_3 − rfn2_3 = 3$ | $rfn2_4 = rfn2_3 − rfn1_4 = 2$ | $TVL_5 = 9 − 1 + 3 = 11$ | |
| STEP 5: $TVL_5$ = -> capture | cpDex = 11  ncDex = 8 | Right = 13 − 2 = 11 | Left = 9 |
| $rfn2_5 = rfn1_4 − rfn2_4 = 1$ | $rfn1_5 = rfn1_4 − rfn2_5 = 2$ | $TVL_6 = 9 − 1 + 2 = 10$ | |
| STEP 6: $TVL_6$-> capture | cpDex = 10 = ncDex = 8 | Right = 11 − 1 = 10 | Left = 9 |
| $rfn2_6 = rfn1_5 − rfn2_5 = 2 − 1 = 1$ | $rfn1_6 = rfn1_5 − rfn2_6 = 1$ | $TVL_7 = 9 − 1 + 1 = 9$ | |
| STEP 7: $TVL_7$-> noncapture | cpDex = 10  ncDex = 9 | $Right_7 = 10$ | $Left_7 = 9 + 1 = 10$ |
| $rfn2_7 = rfn1_6 − rfn2_6 = 1 − 1 = 1$ | $rfn1_7 = rfn1_6 − rfn2_7 = 1$ | cpDex − ncDex = 1 -> EXIT | |

Assuming a capture threshold between 4.2 V and 4.3 V and a range of available pulse strength values between 0.1 V and 5.0 V:

| | | | | |
|---|---|---|---|---|
| STEP 0 (initial condition): | Right = 50 | | | |
| | Left = 1 | | | |
| | $rfn1_0$ = max FibonacciNo | 34 | | |
| | $rfn2_0 = 2^{nd}$ max FibonacciNo | 21 | | |
| | $TVL_1$ = Left − 1 + $rfn1_1$ = $rfn1_1$ = 34 | | | |
| STEP 1: $TVL_1$-> noncapture | ncDex = 34 | $Right_1$ = 50 | $Left_1$ = 1 + 34 = 35 |
| $rfn1_1 = rfn1_0 − rfn2_0 = 13$ | $rfn2_1 = rfn2_0 − rfn1_1 = 8$ | $TVL_2 = 47$ | |
| STEP 2: $TVL_2$-> capture | cpDex = 47  ncDex = 34 | $Right_2$ = 50 − $rfn2_1$ = 42 | Left = 35 |
| $rfn2_2 = rfn1_1 − rfn2_1 = 5$ | $rfn1_2 = rfn1_1 − rfn2_2 = 8$ | $TVL_3 = 42$ | |
| STEP 3: $TVL_3$-> noncapture | cpDex = 47  ncDex = 42 | $Right_3$ = 42 | Left = 35 + 8 = 43 |
| $rfn1_3 = rfn1_2 − rfn2_2 = 3$ | $rfn2_3 = rfn2_2 − rfn1_3 = 2$ | $TVL_4 = 45$ | |
| STEP 4: $TVL_4$-> capture | cpDex = 45  ncDex = 42 | Right = 42 − 2 = 40 | Left = 43 |
| $rfn2_4 = rfn1_3 − rfn2_3 = 1$ | $rfn1_4 = rfn1_3 − rfn2_4 = 2$ | $TVL_5 = 43 − 1 + 2 = 44$ | |
| STEP 5: $TVL_5$ = -> capture | cpDex = 44  ncDex = 42 | $Right_5$ = 40 − 1 = 39 | $Left_5 = 43$ |
| $rfn2_5 = rfn1_4 − rfn2_4 = 1$ | $rfn1_5 = rfn1_4 − rfn2_5 = 1$ | $TVL_6 = 43 − 1 + 1 = 43$ | |
| STEP 6: $TVL_6$-> capture | cpDex = 43  ncDex = 42 | Right = 39 − 1 = 38 | Left = 43 |
| $rfn2_6 = rfn1_5 − rfn2_5 = 0$ | $rfn1_6 = rfn1_5 − rfn2_6 = 1$ | cpDex − ncDex = 1 -> EXIT | |

Further results of steps of a threshold test according to invention for possible capture threshold values are illustrated in the table in FIG. 4.

Pulse strength indices printed in italics indicate loss-of-capture for the assigned pulse strength value. Pulse strength indices printed in bold letters indicate capture for the assigned pulse strength value. From the table, it is apparent, that the duration of the capture threshold test is rather consistent for different capture thresholds.

Although an exemplary embodiment of the present invention has been shown and described, it should be apparent to those of ordinary skill that a number of changes and modifications to the invention may be made without departing from the spirit and scope of the invention.

For example, the concept of capture threshold level testing can be applied to one, two, three or four chamber pacemakers without departing from the claimed invention. In particular in biventricular pacemakers left ventricular capture threshold can be determined by a capture threshold search as disclosed above. This invention can readily be adapted to such devices by following the present teachings. All such changes, modifications and alterations should therefore be recognized as falling within the scope of the present invention.

The invention claimed is:

1. A heart stimulator comprising:
   a. a stimulation pulse generator connected or connectable to at least one stimulation electrode for delivering stimulation pulses to cardiac tissue of a heart chamber, the stimulation pulse generator being adapted to generate stimulation pulses of adjustable stimulation pulse strength,
   b. a sensing stage for sensing a heart parameter indicative of a contraction of a stimulated heart chamber,
   c. a capture detector being connected to the sensing stage and being adapted to:
      (1) evaluate a sensed heart parameter,
      (2) determine whether a stimulation pulse was captured by the stimulated cardiac tissue of the heart chamber or not, and
      (3) provide an output signal, the output signal being either:

(a) a capture signal if analysis of the sensed heart parameter indicates a contraction of the heart chamber following a stimulation pulse of specific stimulation pulse strength, or (b) a non-capture signal if analysis of the sensed heart parameter indicates no contraction of the heart chamber following a stimulation pulse of specific pulse strength, d. a control unit being connected to the stimulation pulse generator and to the capture detector, the control unit:
  (1) comprising means for automatic threshold adaptation, the means for automatic threshold adaptation being configured to perform an automatic iterative threshold search wherein:
    (a) the lowest stimulation pulse strength leading to a capture signal is determined by stepwise increasing or decreasing the adjusted pulse strength in response to a non-capture signal, and
    (b) the automatic iterative threshold search is performed by use of a Fibonacci search algorithm,
  (2) wherein the control unit is configured to control the stimulation pulse generator by adjusting the pulse strength according to a pulse strength value to be applied, the pulse strength value to be applied being determined by the means for automatic threshold adaptation.

2. The heart stimulator of claim 1 wherein:
a. the heart stimulator contains a list of applicable pulse strength values, each of the pulse strength values being assigned to an individual pulse strength index,
b. each pulse strength index is an integer,
c. the list of pulse strength values and the list of pulse strength indices are both monotonic,
d. the list of pulse strength indices begins with a smallest integer being a Fibonacci number which is assigned to the smallest applicable pulse strength,
e. the means for automatic threshold adaptation are adapted to:
  (1) first apply the pulse strength value being assigned to the highest Fibonacci number $rfn1_0$ in the list of integer numbers and to determine a second highest Fibonacci number $rfn2_0$, and
  (2) calculate a next pulse strength index TVL as well as next iteration step parameters $\text{Left}_{n+1}$, $rfn1_{n+1}$ and $rfn2_{n+1}$ in response to the capture detector's output signal as follows:
    (a) in response to a non-capture signal:

$TVL = \text{Left}_n - 1 + rfn1_n$ $\text{Left}_{n+1} = \text{Left}_n + rfn1_n$ $rfn1_{n+1} = rfn1_n - rfn2_n$ $rfn2_{n+1} = rfn2_n - rfn1_{n+1}$ (b) in response to a capture signal:

$TVL = \text{Left}_n - 1 + rfn1_n$ $\text{Left}_{n+1} = \text{Left}_n$ $rfn1_{n+1} = rfn1_n - rfn2_{n+1}$ $rfn2_{n+1} = rfn1_n - rfn2_n$ (3) apply a respective next pulse strength value being assigned to a next pulse strength index TVL until an exit criteria is met, and
    (4) store the latest pulse strength index TVL.

3. The heart stimulator of claim 2 wherein the exit criteria is met if $rfn2_n$ equals 0.

4. The heart stimulator of claim 2 wherein the exit criteria is met if:
a. the most recent pulse strength index assigned to a pulse strength value leading to capture, and
b. the most recent pulse strength index being assigned to a pulse strength value leading to non-capture,
are adjacent.

5. The heart stimulator of claim 2 wherein the exit criteria is met if the pulse strength index TVL equals the smallest applicable pulse strength index minus one, and the smallest applicable pulse strength index is a Fibonacci number.

6. The heart stimulator of claim 2 wherein the smallest integer equals 1 and is assigned to the lowest applicable pulse strength value.

7. The heart stimulator of claim 1 wherein:
a. the heart stimulator contains a list of applicable pulse strength values, each of the pulse strength values being assigned to an individual pulse strength index,
b. each pulse strength index is an integer,
c. the list of pulse strength values and the list of pulse strength indices are both monotonic,
d. the list of pulse strength indices begins with a smallest integer being a Fibonacci number which is assigned to the highest applicable pulse strength,
e. the means for automatic threshold adaptation are adapted to:
  (1) first apply the pulse strength value being assigned to the highest Fibonacci number $rfn1_0$ in the list of integer numbers and to determine a second highest Fibonacci number $rfn2_0$, and
  (2) calculate a next pulse strength index TVL as well as next iteration step parameters $\text{Left}_{n-1}$, $rfn1_{n-1}$ and $rfn2_{n-1}$ in response to the capture detector's output signal as follows:
    (a) in response to a non-capture signal:

$TVL = \text{Left}_n - 1 + rfn1_n$ $\text{Left}_{n+1} = \text{Left}_n$ $rfn2_{n+1} = rfn1_n - rfn2_n$ $rfn1_{n+1} = rfn1_n - rfn2_{n+1}$ (b) in response to a capture signal:

$TVL = \text{Left}_n - 1 + rfn1_n$ $\text{Left}_{n+1} = \text{Left}_n + rfn1_n$ $rfn1_{n+1} = rfn1_n - rfn2_n$ $rfn2_{n+1} = rfn2_n - rfn1_{n+1}$ (3) apply a respective next pulse strength value being assigned to a next pulse strength index TVL until an exit criteria is met, and
    (4) store the latest pulse strength index TVL.

8. The heart stimulator of claim 7 wherein the exit criteria is met if $rfn2_n$ equals 0.

9. The heart stimulator of claim 7 wherein the exit criteria is met if:
a. the most recent pulse strength index assigned to a pulse strength value leading to capture, and
b. the most recent pulse strength index being assigned to a pulse strength value leading to non-capture,
are adjacent.

10. The heart stimulator of claim 7 wherein the exit criteria is met if the pulse strength index TVL equals the smallest applicable pulse strength index minus one, and the smallest applicable pulse strength index is a Fibonacci number.

11. The heart stimulator of claim 7 wherein the smallest integer equals 1 and is assigned to the lowest applicable pulse strength value.

12. The heart stimulator of claim 11 wherein the lowest applicable pulse strength value is 0 Volts.

13. The heart stimulator of claim 12 wherein the list of pulse strength indices TYL is a list of integers from 1 to 50 being assigned to a range of pulse strength values ranging from 0 Volt to 4.9 Volts in steps of 0.1 Volt.

14. The heart stimulator of claim 13 wherein the first pulse strength value to be applied is 3.3 Volts, corresponding to a pulse strength index of 34.

15. The heart stimulator of claim 1 wherein:
a. the sensing stage is adapted to take up myocardial potentials forming a intracardiac electrocardiogram as the heart parameter indicating a contraction of a stimulated heart chamber, and
b. the capture detector is adapted to evaluate the intracardiac electrocardiogram.

16. The heart stimulator of claim 1 wherein:
a. the sensing stage is a ventricular sensing stage connected or connectable to a ventricular sensing electrode, and
b. the stimulation pulse generator is a ventricular stimulation pulse generator connected or connectable to at least one ventricular stimulation electrode.

17. The heart stimulator of claim 1 wherein:
a. the sensing stage is an atrial sensing stage connected or connectable to an atrial sensing electrode, and
b. the stimulation pulse generator is an atrial stimulation pulse generator connected or connectable to at least one atrial stimulation electrode.

18. A heart stimulator comprising:
a. a stimulation pulse generator adapted to generate cardiac tissue stimulation pulses of adjustable stimulation pulse strength,
b. a capture detector adapted to:
(1) receive measurements from stimulated cardiac tissue, and
(2) provide an output signal indicative of whether the stimulated cardiac tissue underwent contraction in response to a cardiac tissue stimulation pulse, the output signals including a:
(a) a capture signal indicative of contraction, and
(b) a non-capture signal indicative of no contraction,
c. a control unit in communication with the stimulation pulse generator and the capture detector, wherein the control unit is configured to perform an iterative threshold search in which the lowest cardiac tissue stimulation pulse strength leading to a capture signal is determined by iteratively increasing or decreasing the adjusted pulse strength in response to a non-capture signal, and the increase and/or decrease in the adjusted pulse strength is dependent on Fibonacci numbers.

19. A heart stimulator comprising:
a. a stimulation pulse generator generating cardiac tissue stimulation pulses, and
b. a sensor detecting whether cardiac tissue receiving the stimulation pulses responds to the stimulation pulses,
c. a controller configured to iteratively adjust the strength of the stimulation pulses to determine the lowest stimulation pulse strength leading to a response by the cardiac tissue, wherein the iterative adjustments are made in dependence on values selected from a Fibonacci sequence.

* * * * *